United States Patent [19]
Paisner

[11] Patent Number: 5,810,740
[45] Date of Patent: Sep. 22, 1998

[54] SYSTEM AND METHOD FOR ANALYZING ELECTROGRAM WAVEFORMS

[75] Inventor: William Lee Paisner, Murrieta, Calif.

[73] Assignee: Heart Rhythm Technologies, Inc., Temecula, Calif.

[21] Appl. No.: 815,672

[22] Filed: Mar. 12, 1997

Related U.S. Application Data

[63] Continuation of Ser. No. 557,686, Nov. 13, 1995, abandoned.

[51] Int. Cl.$^6$ .................................................. A61B 5/0402
[52] U.S. Cl. ............................................. 600/515; 600/523
[58] Field of Search ......................... 128/642, 696–698, 128/702–705, 708, 710; 607/122; 600/509–511, 515–518, 521, 523

[56] References Cited

U.S. PATENT DOCUMENTS

| | | | |
|---|---|---|---|
| 4,522,212 | 6/1985 | Gelinas et al. ........................ | 128/642 |
| 4,577,639 | 3/1986 | Simon et al. .......................... | 128/696 |
| 4,579,119 | 4/1986 | Callaghan . | |
| 4,641,649 | 2/1987 | Walinsky et al. . | |
| 4,649,924 | 3/1987 | Taccardi ................................ | 128/642 |
| 4,660,571 | 4/1987 | Hess et al. . | |
| 4,664,120 | 5/1987 | Hess ...................................... | 128/642 |
| 4,681,117 | 7/1987 | Brodman et al. ..................... | 128/642 |
| 4,777,955 | 10/1988 | Brayton et al. ...................... | 128/642 |
| 4,785,815 | 11/1988 | Cohen .................................. | 128/642 |
| 4,860,762 | 8/1989 | Heumann et al. .................... | 128/702 |
| 4,890,623 | 1/1990 | Cook et al. ........................... | 128/642 |
| 4,940,064 | 7/1990 | Desai . | |
| 4,955,382 | 9/1990 | Franz et al. .......................... | 128/642 |
| 5,025,787 | 6/1991 | Sutherland et al. .................. | 128/698 |
| 5,053,008 | 10/1991 | Bajaj .................................... | 604/104 |
| 5,083,565 | 1/1992 | Parins .................................. | 128/642 |
| 5,123,420 | 6/1992 | Paret .................................... | 128/696 |
| 5,154,501 | 10/1992 | Svenson et al. . | |
| 5,156,151 | 10/1992 | Imran ................................... | 128/642 |
| 5,158,092 | 10/1992 | Glace ................................... | 128/705 |
| 5,172,699 | 12/1992 | Svenson et al. ...................... | 128/705 |
| 5,193,535 | 3/1993 | Bardy et al. . | |
| 5,215,103 | 6/1993 | Desai . | |
| 5,231,995 | 8/1993 | Desai . | |
| 5,233,515 | 8/1993 | Cosman .............................. | 364/413.02 |
| 5,237,996 | 8/1993 | Waldman et al. ................... | 128/642 |
| 5,242,441 | 9/1993 | Avitall ................................. | 606/41 |

(List continued on next page.)

FOREIGN PATENT DOCUMENTS

| | | | |
|---|---|---|---|
| 0 481 684 A2 | 4/1992 | European Pat. Off. ...... | A61B 5/0464 |
| 0 499 491 A2 | 8/1992 | European Pat. Off. ........ | A61N 1/05 |
| 0 573 311 A1 | 12/1993 | European Pat. Off. ...... | A61M 25/01 |
| WO 93/00958 | 1/1993 | WIPO .......................... | A61N 1/06 |
| WO 94/063 | 3/1994 | WIPO .......................... | A61B 5/042 |
| WO 94/22366 | 10/1994 | WIPO .......................... | A61B 5/04 |

*Primary Examiner*—Jeffrey R. Jastrzab
*Attorney, Agent, or Firm*—Fulwider Patton Lee & Utecht, LLP

[57] ABSTRACT

An electrogram analysis system and method for determining the quality of information gathered from electrical signals in biological tissue. The system comprises a catheter having an array of at least two electrodes at its distal end, the electrodes detecting electrical signals emanating from the site of origin and providing relayed signals to a processor. The processor processes the relayed signals into waveforms and computes a quality of the relayed signals. The quality of the relayed signals is used to select higher quality signals for further analysis, such as site of origin determination and mapping. The relayed signals from the electrodes may also be used to determine a quality for a particular electrode channel. When the invention is used in cardiac applications, the relayed signal quality may comprise two components—a channel quality and a beat quality. The channel quality represents the value of information received from a particular electrode and channel, while the beat quality represents the value of a particular heart beat across all channels. The signal quality is displayed to the user. In cardiac applications, the channel quality can be displayed in a format corresponding to the shape of the electrode array, with channel quality from each electrode positioned in a corresponding position on the display. The display may also show the waveforms of the signal, such as the heart beat waveform in a cardiac procedure.

25 Claims, 10 Drawing Sheets

U.S. PATENT DOCUMENTS

| | | | |
|---|---|---|---|
| 5,255,678 | 10/1993 | Deslauriers et al. | 128/642 |
| 5,255,679 | 10/1993 | Imran | 128/642 |
| 5,263,493 | 11/1993 | Avitall | 607/122 |
| 5,279,299 | 1/1994 | Imran | 128/642 |
| 5,281,213 | 1/1994 | Milder et al. | 606/15 |
| 5,293,869 | 3/1994 | Edwards et al. | 128/642 |
| 5,295,484 | 3/1994 | Marcus et al. | 128/660 |
| 5,297,549 | 3/1994 | Beatty et al. | 128/642 |
| 5,364,352 | 11/1994 | Cimino et al. | 604/95 |
| 5,365,926 | 11/1994 | Desai | 128/642 |
| 5,383,917 | 1/1995 | Desai et al. | |
| 5,397,339 | 3/1995 | Desai | 607/116 |
| 5,433,198 | 7/1995 | Desai | 128/642 |
| 5,456,261 | 10/1995 | Luczyk | 128/702 |
| 5,458,115 | 10/1995 | Sivard et al. | 128/708 |
| 5,469,857 | 11/1995 | Laurent et al. | 128/696 |

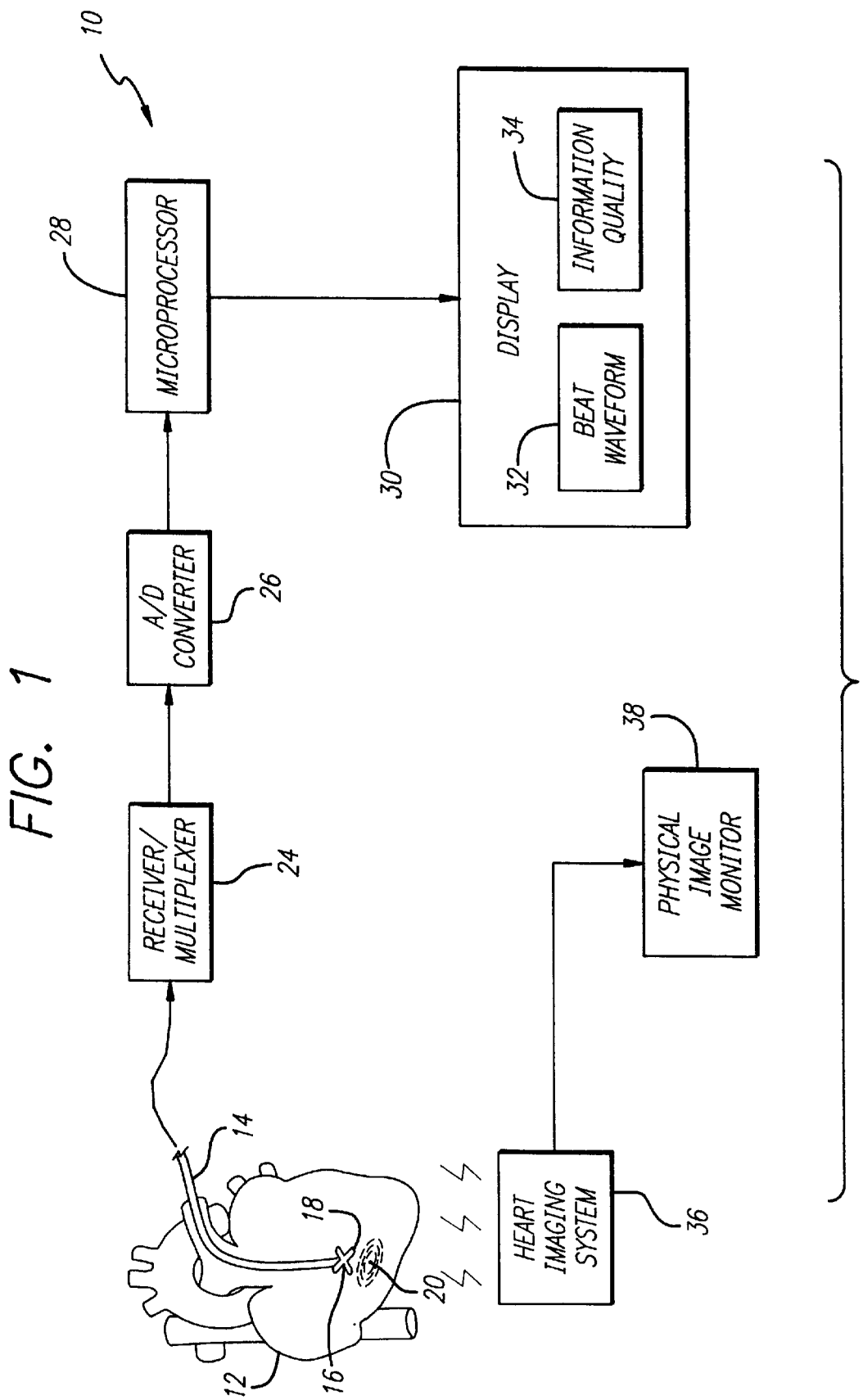

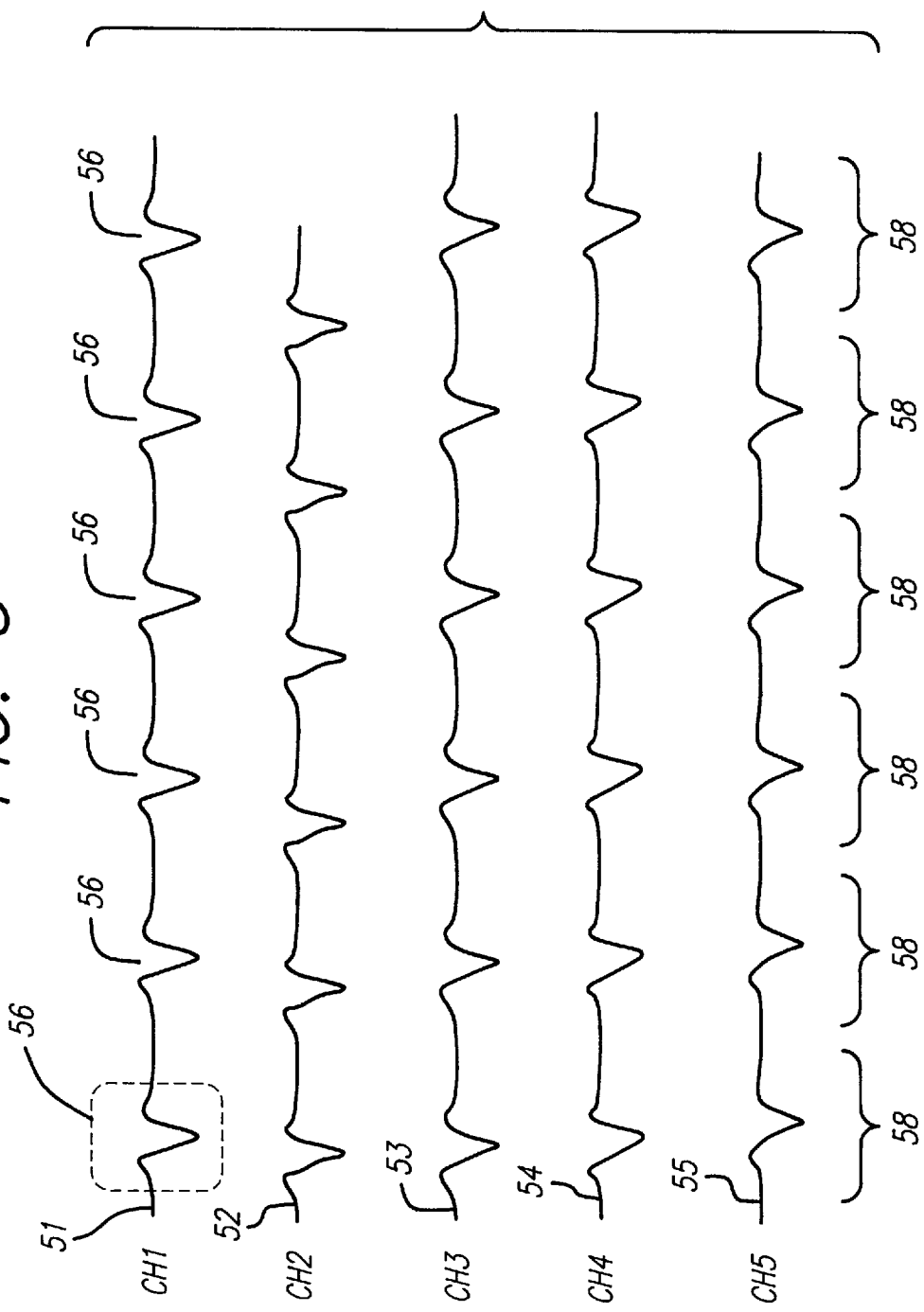

SYSTEM AND METHOD FOR ANALYZING ELECTROGRAM WAVEFORMS

This application is a continuation of application Ser. No. 08/557,686 filed Nov. 13, 1995 now abandoned.

FIELD OF THE INVENTION

The invention relates generally to medical devices and, more particularly, to a system and method for analyzing the quality of heart electrogram waveform signals.

DESCRIPTION OF RELATED ART

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia.

Electrophysiological ("EP") ablation is a procedure often associated in treating cardiac arrhythmia. This procedure typically involves applying sufficient energy to the interfering tissue to ablate that tissue, thereby removing the irregular signal pathway.

Once the origination point for the arrhythmia has been located in the tissue, the physician may use an ablation procedure to destroy the tissue causing the arrhythmia in an attempt to remove the electrical signal irregularities and restore normal heart beat or at least an improved heart beat. However, determining the origination point of the arrhythmia is difficult. Various techniques are used to determine the precise location of the interfering tissue and guide a therapeutic device to the site of the interfering tissue for treatment.

One technique for locating an arrhythmia origination point is localized mapping of the electrical signal irregularities to identify the site of origin. In such a technique, one or more electrodes are used to map the site of origin. Electrodes located closer to the site of origin will generally detect electrical signals from the site earlier than electrodes farther away. By comparing the electrical signal arrival times at different electrode locations, the location of the site of origin can be determined.

The electrical signal is typically relayed by the electrodes to a microprocessor for analysis and mapping. However, various sources of interference can degrade the quality of the signal relayed by the electrode. One or more electrodes can be in poor contact with the tissue. Electrodes can become damaged or encrusted with biological particles, and data gathered by such a degraded electrode may be inaccurate. Additionally, electrical noise sources can cause otherwise accurate electrodes to relay inaccurate and/or misleading information.

Another problem is selecting a properly representative heart beat waveform. Detected waveforms vary from heartbeat to heartbeat. Analysis of a heartbeat waveform that is not properly representative can result in degraded results and information.

Hence, those skilled in the art have recognized the need for a system and method for determining the quality of the waveform information provided by the electrodes, and to discriminately select properly representative signals. Additionally, those skilled in the art have recognized a need to relay quality information to the user in a format that is easily interpreted. The present invention fulfills these needs and others.

SUMMARY OF THE INVENTION

Briefly and in general terms, the present invention provides a system and a method for determining the quality of information gathered from a site of electrical signals in biological tissue. The system comprises a catheter having an array of at least two electrodes at its distal end, the electrodes detecting electrical signals emanating from the site of origin and providing relayed signals to a processor. The processor processes the relayed signals into waveforms and computes a quality of the relayed signals.

In one aspect, there is provided a system for analyzing electrical signals in biological tissue that comprises a catheter having a proximal end and a distal end, said catheter having an array of at least two electrodes at the distal end, the electrodes detecting said electrical signals emanating from the site of origin and providing relayed signals representative of the electrical signals detected at the electrode position. A receiver is coupled to the catheter and receives the relayed signals provided by the electrodes and a processor processes the relayed signals received from the receiver into waveforms and computes a quality of the relayed signals as a result of said processing.

In a more detailed aspect, the processor categorizes the relayed signals into beat signals when the biological tissue is heart tissue. Additionally, in further detail, each electrode has an electrical channel along which the electrode transmits relayed signals to the receiver, and the processor selects a set of contemporaneous beat signals, said contemporaneous set comprising one beat signal from each of two or more channels, to comprise an aligned beat signal.

In yet a further aspect, the processor computes a channel quality and a beat signal quality, said channel quality and said beat signal quality comprising the relayed signal quality.

In additional aspects, the processor determines a quality metric for each beat signal in a channel, selects from a channel the set of beat signals whose quality metrics are most closely clustered, averages the quality metrics of the selected beat signals, and determines channel quality as a function of the quality metrics of all beats and the computed average quality metric of the selected beats. Further, the processor determines a quality factor for one or more beat signals as a function of the proximity of the quality metric of the beat signal to the average quality metric for the channel. The processor groups into aligned beat signals those beats across channels which are aligned in time. An aligned beat signal quality is calculated by the processor for at least one aligned beat signal as a function of the quality factors of the beat signals comprising the aligned beat signal. In a further more detailed aspect, the processor calculates the aligned beat signal quality as the sum of the quality factors of the beat signals comprising the aligned beat signal.

In other aspects, a display interactively displays the quality of relayed electrical signals. The display comprises a plurality of quality representations, wherein one or more of the quality representations each displays the quality of a relayed signal received from a particular electrode. In another aspect, the plurality of quality representations are arranged in a pattern corresponding to the shape of the electrode array.

Other aspects and advantages of the invention will become apparent from the following detailed description and accompanying drawings, illustrating by way of example the features of the invention.

BRIEF DESCRIPTION OF THE DRAWINGS

FIG. 3 is a diagram showing multichannel beat waveforms;

DETAILED DESCRIPTION OF THE PREFERRED EMBODIMENTS

Figures 1, 4:
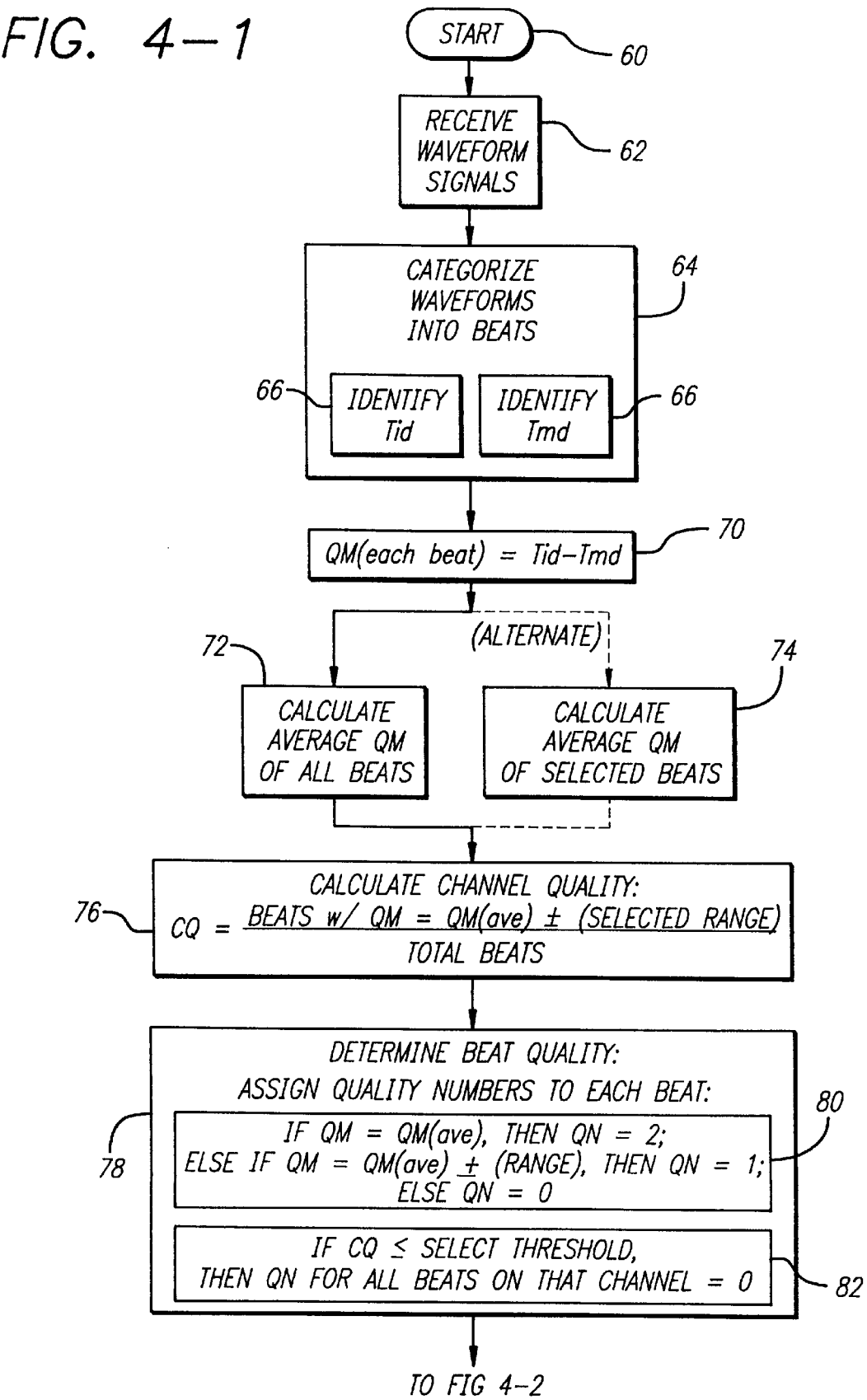
FIG. 1 is a schematic diagram illustrating a mapping system incorporating aspects of the invention.
FIG. 4 is a flow diagram showing the steps for cardiac mapping according to one embodiment of the present invention.
Figures 2, 4:
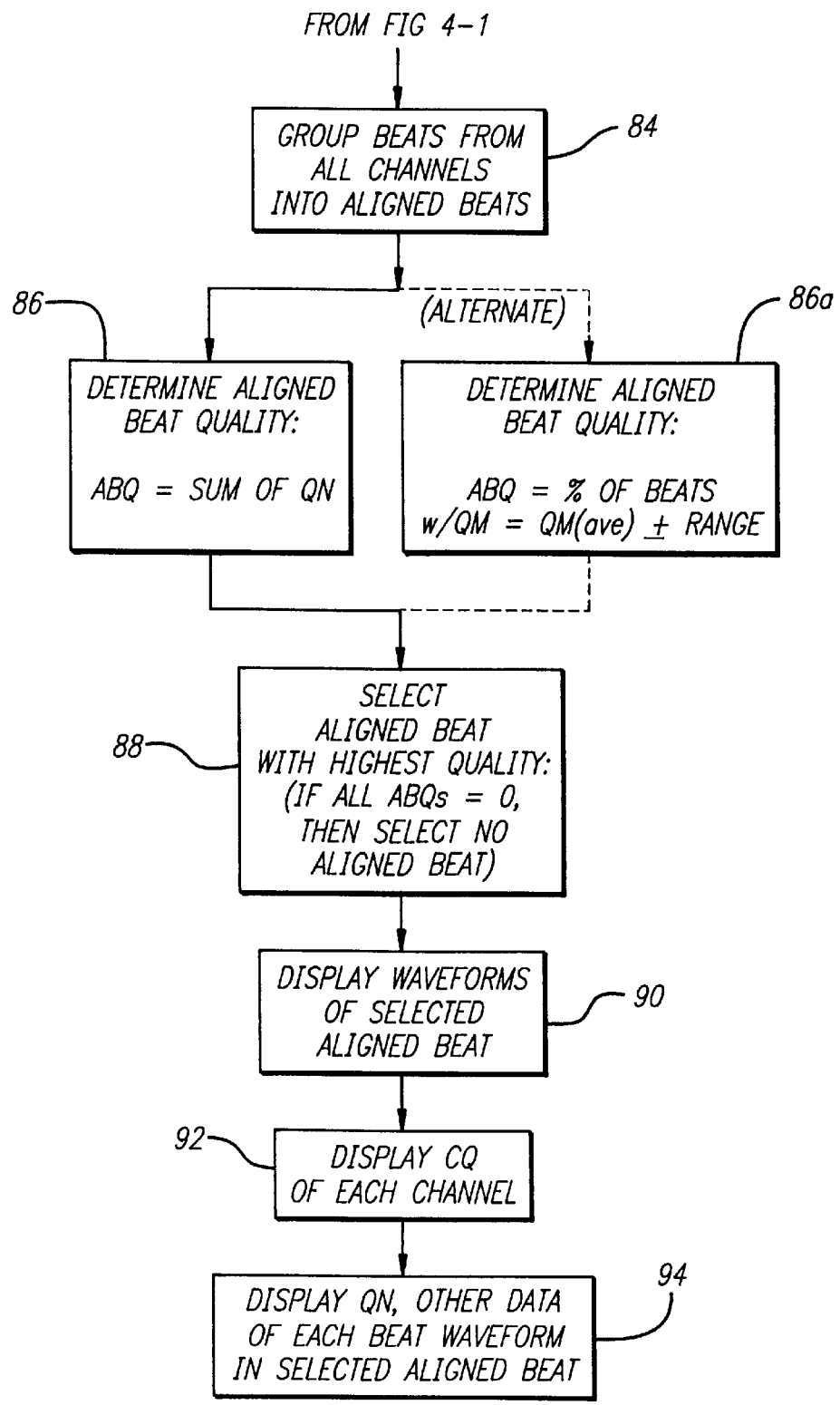

Referring now to the drawings with more particularity, wherein like reference numerals designate like or corresponding elements among the several views, there is shown in FIG. 1 a system 10 for mapping electrical signals in biological tissue and for determining the quality of the information provided. In the embodiment of FIG. 1, the subject tissue is the tissue of a heart 12. The catheter 14 includes an electrode array 16 comprising a plurality of electrodes 18. In the local site spanned by the electrode array 16, the electrodes 18 detect intraelectrocardiac signals emanating from a site of origin 20. The intraelectrocardiac signals are relayed from the electrodes through a multi-channel lead connector 22 and receiver/multiplexer 24 to an A/D convertor for digitization. The digitized relayed signals are routed to a microprocessor 28. The microprocessor 28 analyzes the relayed signals to determine the quality of the information from the relayed signals. The microprocessor may also process the relayed signals into beat waveforms. Information regarding the heartbeat signals is forwarded to a display 30. The display in the embodiment shown includes a beat waveform display 32 and an information quality display 34.

The microprocessor 28 also analyzes the signals to determine the direction of the site of origin 20 with respect to the electrode array 16. The relayed signals are processed by the microprocessor 28 to provide real-time information such as arrival times of intracardiac signals at each electrode 18. The electrodes located closer to the site of origin 20 will generally detect these electrical signals earlier than electrodes farther away. By comparing the arrival times at each electrode, the direction of the site of origin 20 of the electrocardiac signals can be determined. This information can be used to guide the catheter 14 (or another device) to the site of origin.

The embodiment shown also provides a physical display of the location of the electrode array 16 in the heart 12. An image of the heart 12 and catheter 14 is provided by a heart imaging system 36, such as a fluoroscope, to a video monitor 38 or other display.

Figure 2:
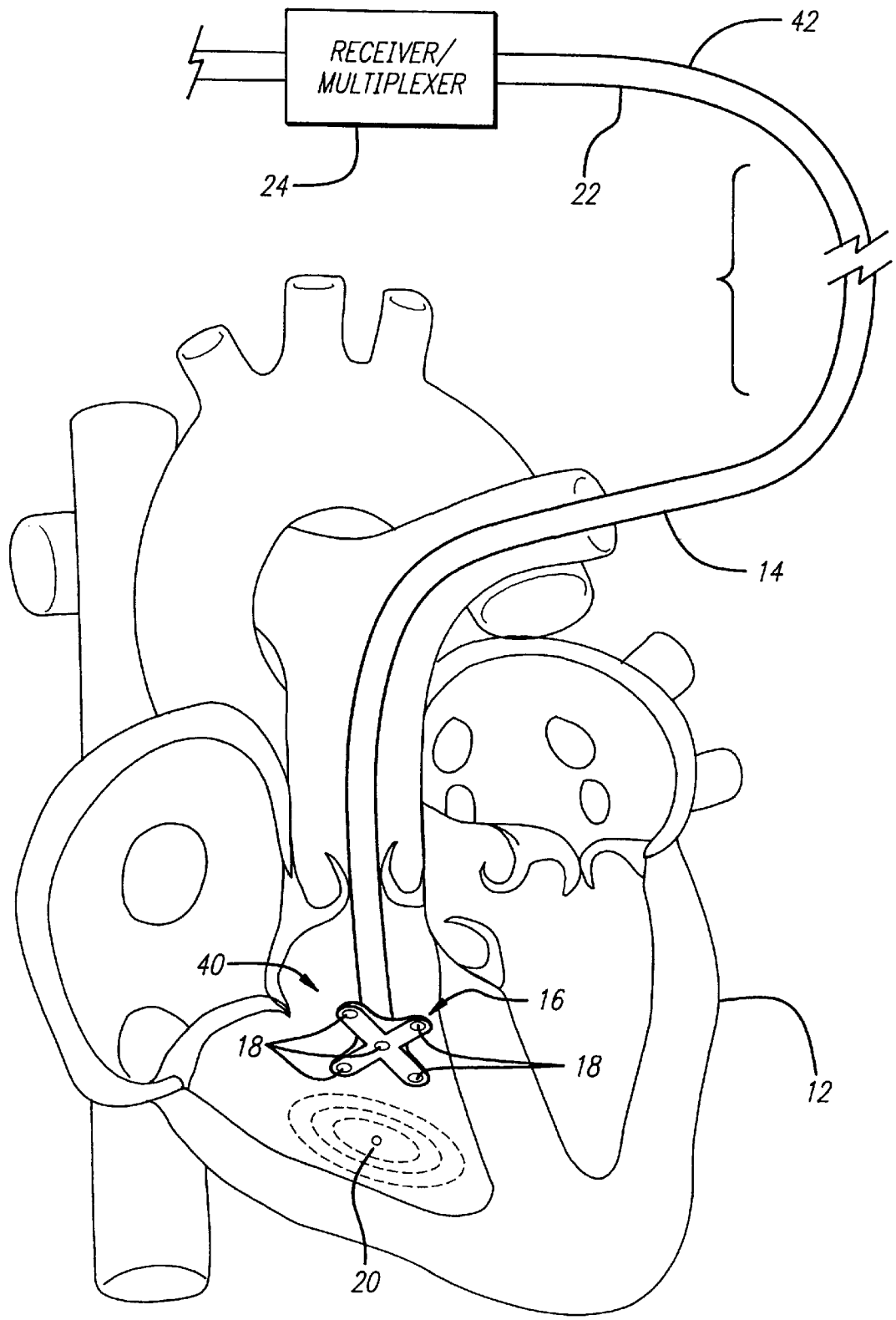
FIG. 2 is a diagrammatic view of a human heart in partial cross section showing an multi-electrode catheter disposed internally therein in a deployed position.

FIG. 2 is a diagrammatic view of a human heart in partial cross section showing an multi-electrode catheter 14 disposed internally therein. The catheter 14 performs localized mapping of the endocardial tissue. During heart mapping procedures, the catheter 14 is typically introduced percutaneously into the heart through a blood vessel such as a femoral vein.

The catheter 14 includes a distal end 40 and a proximal end 42. The proximal end 42 is connected to the receiver 24 via a multichannel lead connector 22. The distal end 40 includes the electrode array 16, which in the embodiment shown comprises an x-shaped array of five electrodes 18.

Figure 2A:
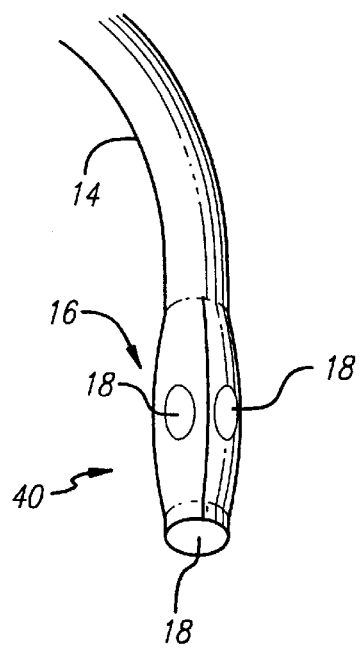
FIG. 2a is a partial elevation view of a multi-electrode catheter showing the electrode array in the retracted position.

FIG. 2a shows the catheter 14 with the electrode array 16 in the retracted position. The electrodes 18 are retracted to allow the distal end 40 to be introduced through relatively narrow passages into the heart. When the distal end 40 enters the heart, the electrodes 18 are deployed to assume the x-shaped electrode array 16 shown in FIG. 2. A catheter with an electrode array usable as discussed above is shown in U.S. Pat. No. 4,940,064 to Desai, incorporated herein by reference.

FIG. 3 is a diagram showing multichannel beat waveforms 51, 52, 53, 54, and 55 derived from signals relayed from a five-electrode catheter array over a defined period. Each waveform 51, 52, 53, 54, and 55 corresponds to electrical signals received from channels 1 through 5, respectively. The waveforms 51, 52, 53, 54, and 55 are categorized into beats 56. Beat categorization may be performed by a beat detection algorithm, of which several are known in the art.

Depending on the heart rate and defined time period, there is typically more than one beat captured per channel over the defined period. In the period shown in FIG. 3, there are six heart beats captured per channel.

Figure 3A:
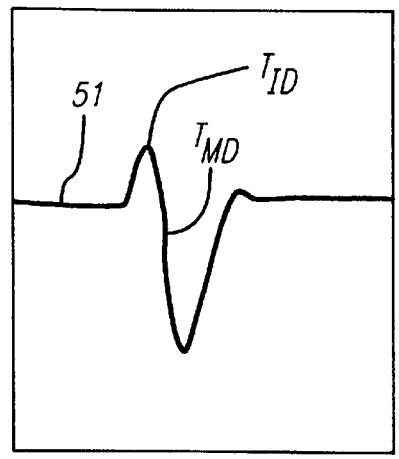
FIG. 3a is a diagram showing a selected beat waveform.

FIG. 3a shows the first beat from waveform 51 corresponding to Channel 1. In the embodiment shown in FIG. 3a, further processing identifies two reference points for each beat 56 on a particular waveform. The first reference point is identified using the initial downslope method, which is an industry standard. This first reference point, also known as the Initial Downslope point or $T_{id}$, is the point where the waveform first begins to descend. The second reference point is identified via the so-called Maximum Downslope Method, which is also an industry standard. This second reference point, the so-called Maximum Downslope point or $T_{md}$, is the point where the waveform reaches its maximum downslope.

The reference points $T_{id}$ and $T_{md}$ can be used to identify beats from separate channels that are aligned in time. The identified beats can be grouped into aligned beats 58, with each aligned beat 58 comprising a beat from each channel. By analyzing the quality of the beats 56 in each aligned beat 58, a preferred aligned beat can be selected for further analysis (such as determining the direction of the site-of-origin) and for display to the user.

FIG. 4 shows the steps for determining signal quality and beat quality in cardiac mapping according to one embodiment of the invention. The process is started at step 60. At step 62, multiple waveforms are received, with each waveform corresponding to signals received by a particular electrode and channel. At step 64, the processor categorizes the waveforms into beats. In the embodiment shown, beat categorization includes step 66, which is identifying the Initial Downslope point or $T_{id}$, and step 68, which is identifying the Maximum Downslope point or $T_{md}$.

At step 70, a quality metric is determined for each beat on each channel. In the embodiment shown, the quality metric (QM) for each beat equals the time difference of the two reference points $T_{id}$ and $T_{md}$.

At step 72, the average quality metric ("$QM_{ave}$") is determined for the beats from each channel. $QM_{ave}$ may be determined using standard averaging techniques.

Step 74 shows an alternative to step 72, wherein $QM_{ave}$ is determined as the average QM of a group consisting of only a select number of the beats from each channel. In such an embodiment, the beats from each channel are examined to determine the most tightly clustered group of beats, i.e., the group of beats having the most similar QMs. The most tightly clustered group may comprise a determined percentage of the beats on the channel, such as 50 percent. Step 74, i.e., determining $QM_{ave}$ of selected beats, may be a preferred alternative to step 72 depending on the particular application. For example, in determining a tachycardia site, selecting a group of beats with similar QMs increases the chances that the selected beats are representative tachycardia beats.

Figure 5A:
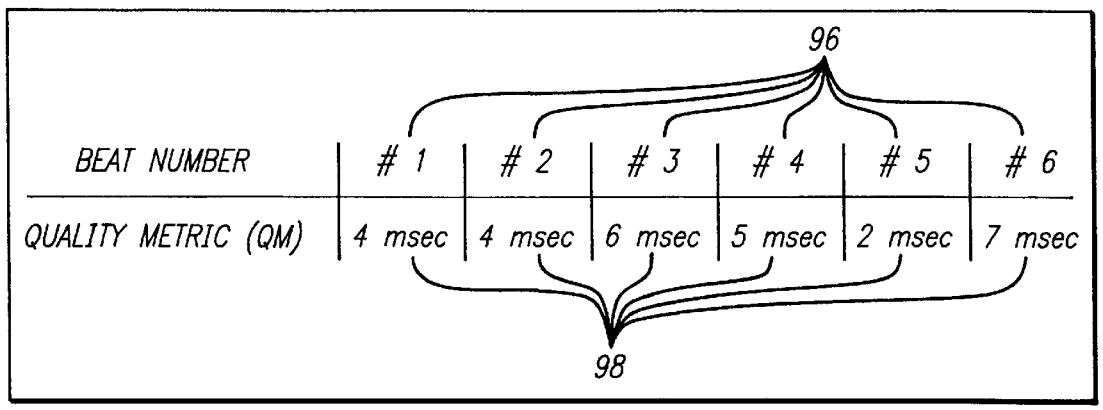
FIG. 5a is a table showing sample quality metrics for different beat waveforms.
Figure 5B:
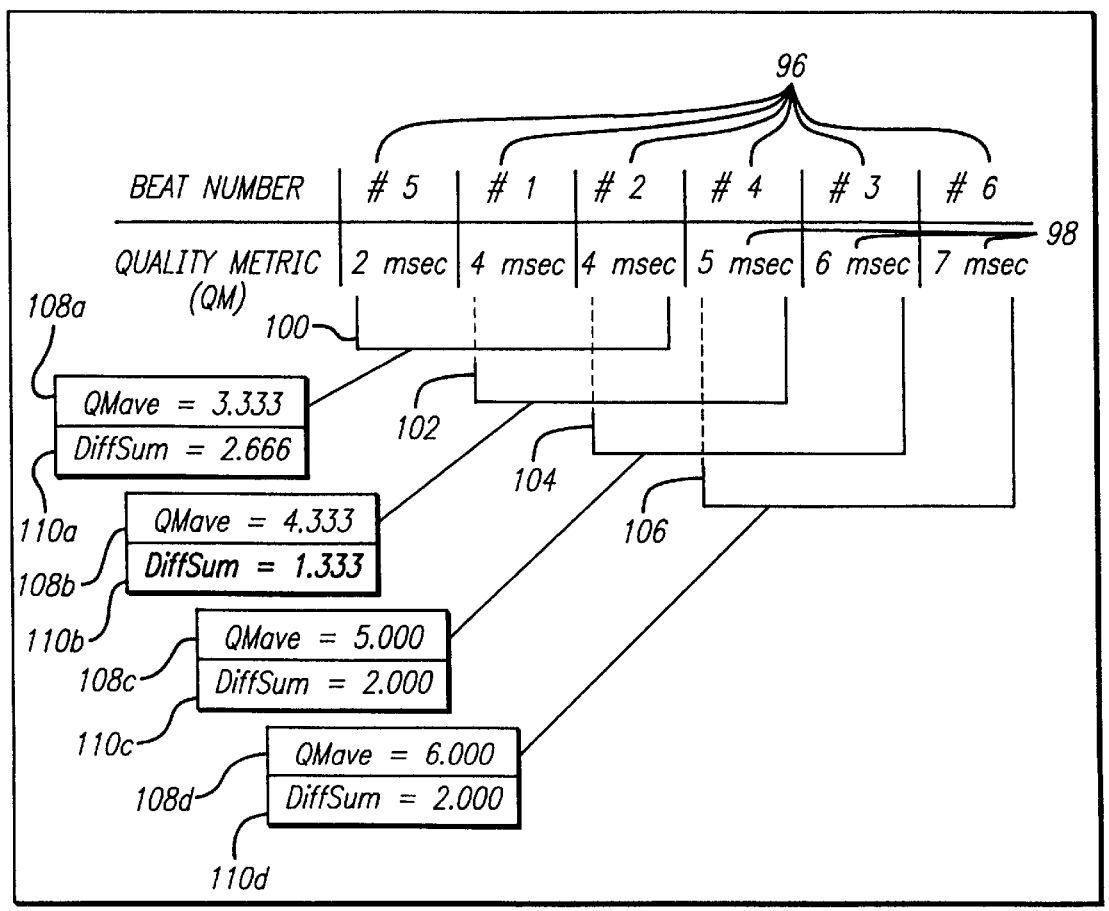
FIG. 5b is a table showing sample quality metrics and selected groupings of different beat waveforms.

One embodiment of a methodology for selecting the most tightly clustered group of beats is shown by way of example in FIGS. 5a and 5b. In the sample in FIGS. 5a and 5b, the 50% of beats in a six beat sample that have the most tightly clustered QM values is desired. The beats are initially shown in FIG. 5a in chronological order, with each beat having a beat number 96 from 1–6 corresponding to that chronological order. The QM 98 of each beat is also shown. As shown in FIG. 5b, the beats are re-ordered according to their QM values 98, i.e., starting from the beat with the lowest QM and going up to the beat with the highest QM.

After the beats are ordered according to QM values 98, the beats are grouped into three-beat groups, corresponding to 50% of the total beats. The first group 100 is the three beats having the lowest QMs, the second group 102 is the three beats having the next lowest QMs, the third group 104 has the next lowest QMs, and the fourth group 106 has the highest QMs. Each of these 3-beat groups will be assessed to determine the similarity of the beats within the 3-beat group.

The first 3-beat group 100 is selected, and the $QM_{ave}$ 108a is calculated for that group. The differences between the QM of each of the three beats in the first group 100 and the $QM_{ave}$ 108a of that group are determined, and the sum of the absolute values of these differences (DiffSum) 110a is determined. In the sample of FIG. 4b, $QM_{ave}$ 108a of the first group is 3.333, and the sum of the differences (Diffsum) 110a is 2.666.

The above process is repeated for the second 102, third 104, and fourth 106 groups, determining $QM_{ave}$ 108 and DiffSum 110 for each group. The three-beat group having the lowest DiffSum 110, which in the sample shown in FIGS. 5a and 5b is the DiffSum 110b of the second group 102 with a value of 1.333, is selected. The $QM_{ave}$ of this selected group is the $QM_{ave}$ determined in alternative step 74. Accordingly, where alternative step 74 is applied, the $QM_{ave}$ of the selected group would be used for the analysis performed in steps 76–86a of FIG. 4.

Although in the embodiment of FIG. 5 QM is the factor used to determine the most tightly clustered group of beats, other signal parameters representing selected characteristics of the relayed signal might also be used. Such signal parameters might include waveform characteristics such as waveform pulse height, waveform pulse width, etc.

Referring again to FIG. 4, at step 76 the channel quality is determined as a function of the consistency and repeatability of the beat signals from a particular channel. In the embodiment shown, the channel quality ("CQ") of a particular channel is equal to the "good" selected beats from the channel divided by the total beats from the channel. The so-called "good" beats are beats whose QM is within a selected range of $AM_{ave}$ for the channel. In one embodiment, the selected range is 1 msec, so that a "good" beat is a beat whose QM equals $AM_{ave}$ plus or minus 1 msec.

CQ is particularly valuable where an electrode or channel link is malfunctioning. A malfunctioning electrode or channel link is unlikely to relay consistent and repeatable beat signals. Where consistency and repeatability are degraded on a particular channel, the information from that channel can be discarded, as shown in step 80 which is discussed in greater detail below, or weighted accordingly.

In step 78, a beat quality is determined for each beat on a channel. In step 78, which comprises steps 80 and 82, the beat quality equals a quality number (QN). Quality numbers range from 0 to 2. As shown at step 80, if the QM of a beat equals $QM_{ave}$, then that beat receives a QN of 2. If the QM does not equal $QM_{ave}$ but is within a selected range of $QM_{ave}$, such as 1 msec, then that beat receives a QN of 1. If the QM is not within the selected range of $QM_{ave}$, then that beat receives a QN of 0.

It is generally undesirable to use any beat signals from a low quality channel, i.e., a channel having a channel quality of less than a selected threshold, as was discussed with respect to step 76. Accordingly, step 82 shows that a QN of zero is assigned to all beat signals from any channel having a CQ of less than a selected threshold, which in the embodiment shown is 50 percent.

At step 84, beats from all channels are grouped into aligned beats. Aligned beats 58 were previously shown in FIG. 3. The beats may be grouped using various methodologies. For example, an aligned beat may comprise all beats having defining characteristics, such as reference point $T_{id}$, falling within a maximum time range of each other.

At step 86, an aligned beat quality is determined for each aligned beat. In the embodiment shown, the aligned beat quality is a function of the repeatability and consistency of each beat signal in the aligned beat. As shown in step 86, aligned beat quality ("ABQ") equals the sum of the quality numbers QN from each beat signal comprising the aligned beat.

As an optional method for determining an aligned beat quality, ABQ may be determined as a percentage. As shown in step 86a, which is an alternative step to step 86, ABQ is determined as the percentage of beat signals comprising the aligned beat whose QMs are within a selected range (such as 1 msec) of their corresponding $QM_{ave}$, as was discussed above with respect to step 80. Thus, rather than having an aligned beat quality that is an integer value, the aligned beat quality is a percentage value.

At step 88, the aligned beat having the most favorable quality is selected for further analysis and processing. In the embodiment shown, the aligned beat having the highest ABQ is selected. However, if no aligned beat has an ABQ of greater than zero, then no aligned beat is selected.

The quality information is then displayed to the user. At step 90, the waveforms of the selected aligned beat is displayed. At step 92, the channel quality of each channel is displayed. At step 94, the QN of each beat in the selected aligned beat is displayed.

Figure 6:
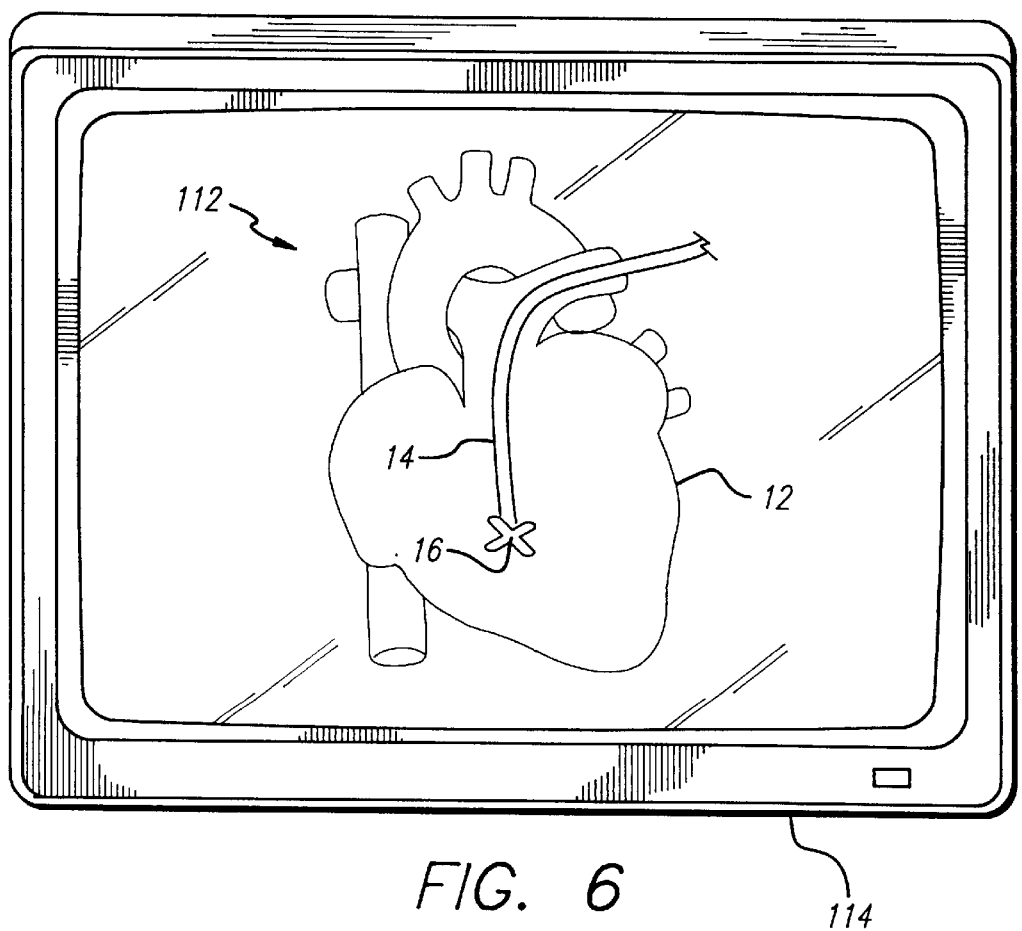
FIG. 6 is a sample display on a video monitor showing an image of the heart and the electrode array.

FIG. 6 is a sample display 112 on a video monitor 114 showing an image of the heart 12 and the location of the electrode array 16. The electrode array 16 is shown at its respective position within a patient's heart 12. Two such displays 112, from orthogonal planes, could be provided during a procedure, thus providing positioning and mapping information to assist the user in guiding the electrode array 16 or an ablation device to the site of origin. The image of the heart 12 and catheter 14 may be a graphical image provided by a heart imaging system, such as the heart imaging system 36 discussed above with respect to FIG. 1. Such a heart imaging system may be a fluoroscope or other imaging device, and may be used in conjunction with radio-opaque markers on the catheter to indicate catheter and electrode array orientation. The heart imaging system may further display information regarding the direction of the site of origin within the heart 12.

Figure 7:
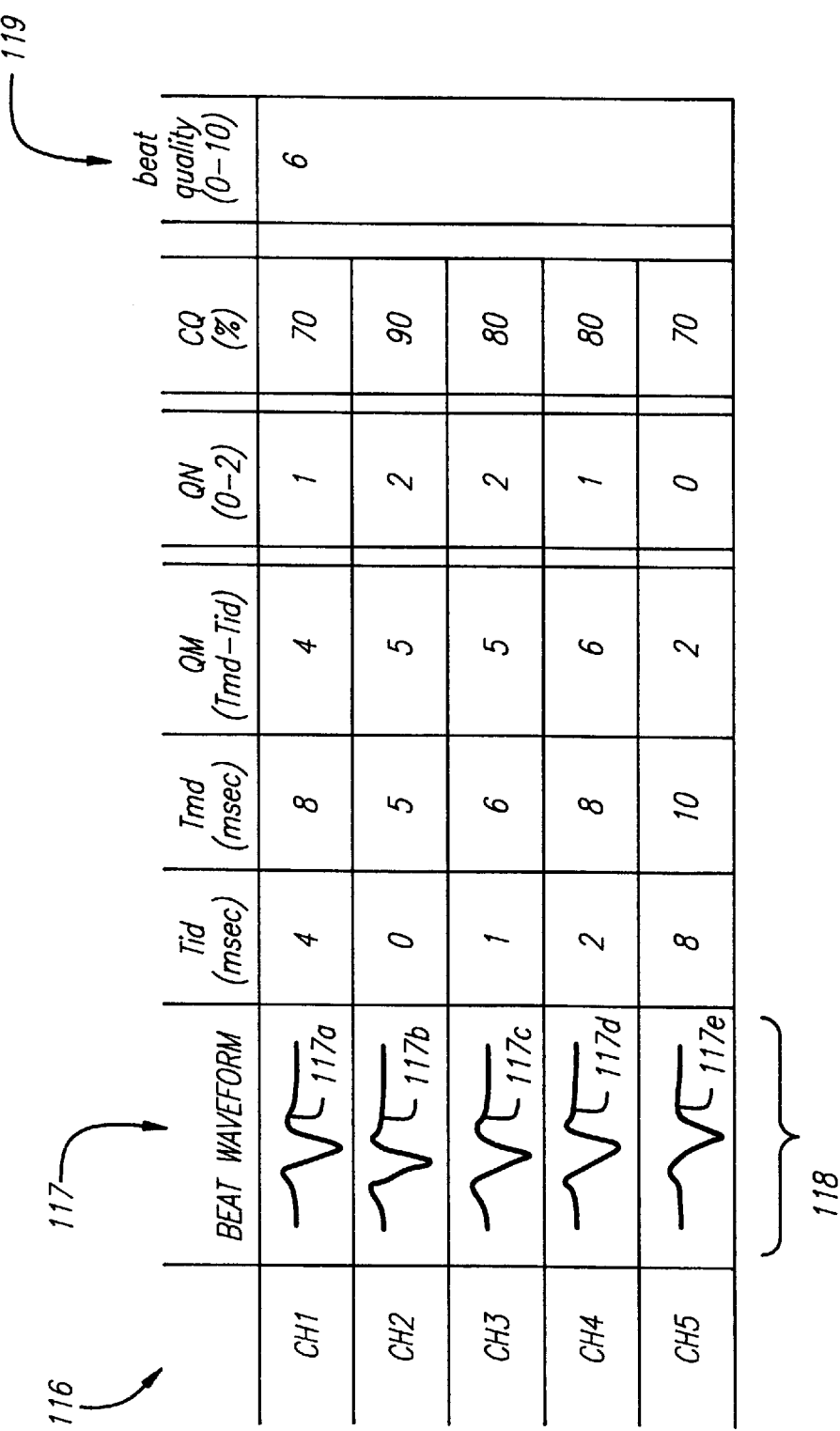
FIG. 7 is a table and diagram showing various waveform parameters and signal quality.

FIG. 7 is a table 116 showing multiple beat waveforms 117 comprising a single selected aligned beat 118, with each of the beat waveforms 117 obtained from a separate channel as described with respect to FIG. 3. For each beat waveform 117, the table includes selected reference points, which in the embodiment shown are $T_{id}$ and $T_{md}$. In the embodiment shown, for ease of reference the earliest $T_{id}$ of all beat waveforms is set at zero, and all other $T_{id}$ values for the other beat waveforms, as well as all $T_{md}$ values, are presented relative to the initial $T_{id}$. In FIG. 7, the beat waveform 117b of channel 2 has the earliest $T_{id}$, which is shown with a value of 0.

FIG. 7 also shows the quality metric QM and quality number QN for each beat, as well as the channel quality CQ for each waveform's channel. Note that QN and CQ are calculated based on all the beats on a particular channel, not just the particular beat comprising the aligned beat shown in the table of FIG. 7.

FIG. 7 also shows a quality indicator 119 for the aligned beat, which in the embodiment shown is the sum of the quality numbers QN from each beat comprising the aligned beat. In an alternative embodiment, the quality indicator may be determined as a percentage of the beats in the aligned beat that have a QM within a selected range, as was discussed above with respect to FIG. 4, step 86a.

Figure 8:
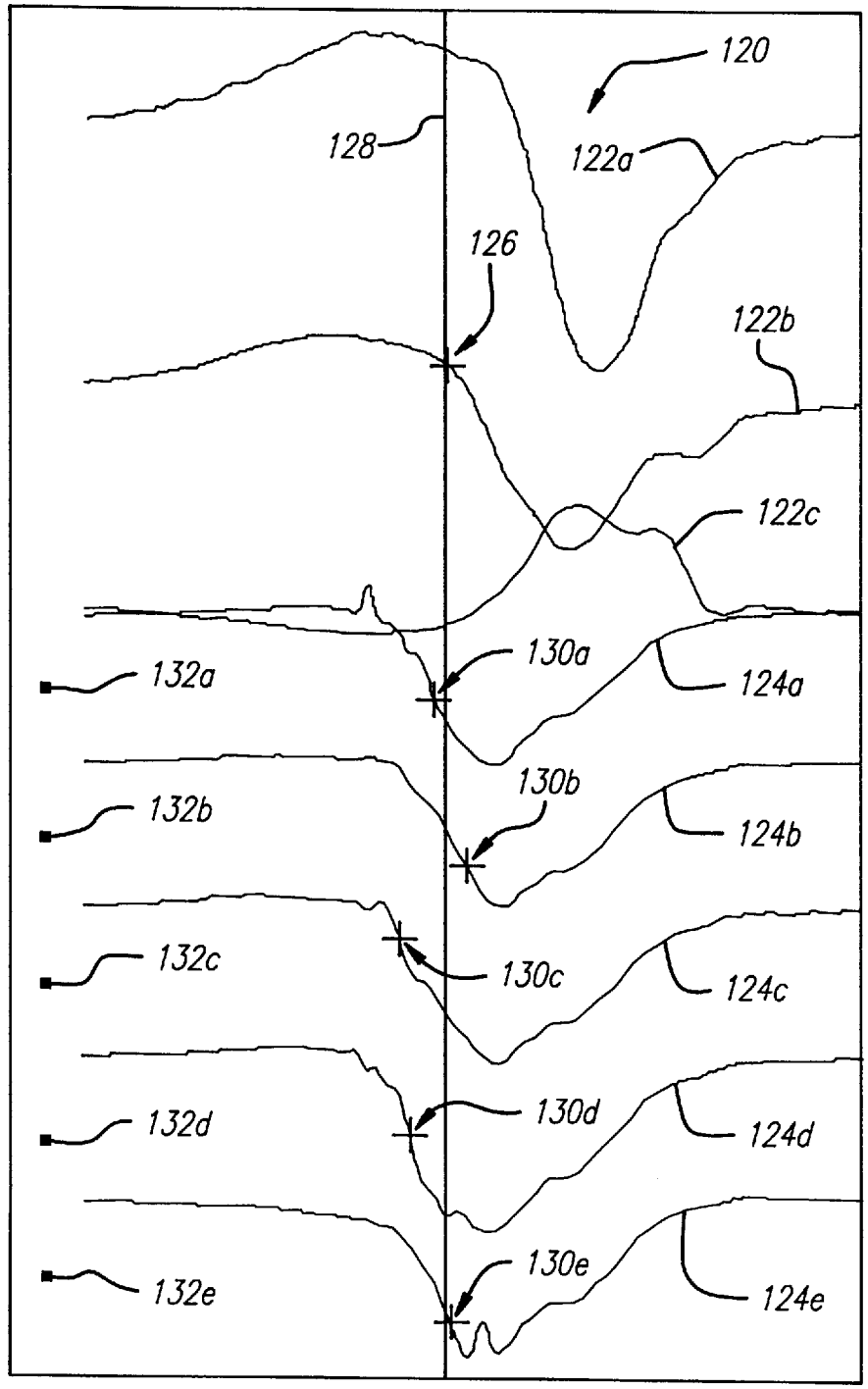
FIG. 8 is a sample display on a video monitor showing channel quality and signal waveforms.

FIG. 8 shows a display 120 of selected aligned beat waveforms 122, 124 and channel quality. The display 120 includes three ECG beat waveforms 122 and five catheter electrode beat waveforms 124. Each of the catheter electrode beat waveforms 124 corresponds to a different channel of a 5-electrode x-shaped array. Catheter beat waveform 124a corresponds to the first channel from the 5-electrode array, which in common convention corresponds to the center electrode of an x-shaped electrode array. Each of catheter beat waveforms 124b, 124c, 124d, and 124e corresponds to an outer electrode in the x-shaped electrode array.

In the particular embodiment of FIG. 8, the earliest $T_{id}$ of the three ECG waveforms, which in this example occurs in the second of the three ECG waveforms at point 126, is selected as the zero time reference 128, also known as $T_0$. In the example of FIG. 8, the zero time reference 128 is indicated by a vertical line passing through $T_{id}$ of the second ECG waveform. The $T_{md}$ 130 of each catheter waveform is also shown. In FIG. 8, the $T_{md}$'s 130a, 130c, and 130d of the first, third, and fourth waveforms (respectively) occur prior to the zero reference 128. Accordingly, in the selected time frame of reference, the arrival times (i.e., $T_{md}-T_0$) of these channels have a negative value. The second and fifth waveforms' arrival times 130b and 130e occur after the zero reference 130, so that these arrival times 130b and 130e have a positive value.

The display 120 of FIG. 8 further includes a channel quality indicator, which in the embodiment shown is a colored square 132, for each channel. The channel quality square 132 changes between red, yellow, and green, depending on the particular channel quality. In one embodiment, a green quality square represents a channel quality percentage of greater than 85%, a yellow quality square represents a channel quality percentage of 70 to 85%, and a red quality square represents a channel quality percentage of less than 70%. Note that, as was discussed above with respect to FIG. 4, the channel quality is a function of several beats on the same channel, not just of the single selected beat waveform shown for each channel in FIG. 8.

With the display of FIG. 8, the user can see representative ECG waveforms 122 aligned in time with select waveforms 124 from each channel, while simultaneously viewing a channel quality indicator in the form of a colored square 132.

Figure 9:
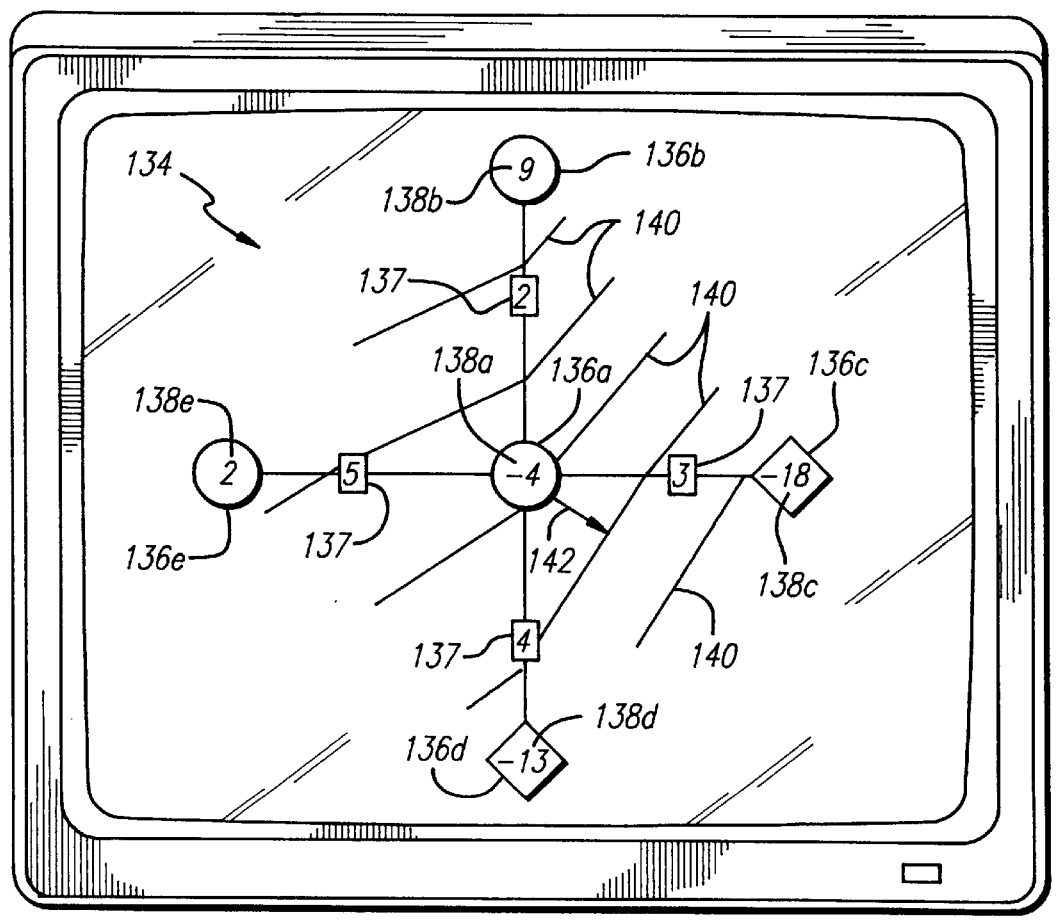
FIG. 9 is a sample display on a video monitor showing beat quality.

FIG. 9 shows a display 134 of beat quality and signal arrival times, with the display having a pattern corresponding to the shape of an x-shaped five-electrode array. The beat quality display 134 comprises five indicia 136, with each indicia including the beat quality of a particular electrode. For example, the center indicia 136a in the beat quality display 134 shows the beat quality corresponding to the central electrode, in this embodiment corresponding to channel 1, in an x-shaped five-electrode array. The outer indicia 136b, 136c, 136d, and 136e correspond to the outer electrodes, which in this embodiment correspond to channels 2, 3, 4, and 5 as shown by the channel indicators 137.

Inside each indicia 136 is a number 138 corresponding to the arrival time of the selected beat waveform from the corresponding channel, where arrival time is defined as $T_{md}-T_0$. These selected beat waveforms are shown in the display of FIG. 8, which in a preferred embodiment is shown in proximity to the display of FIG. 9.

In the embodiment of FIG. 9, the shape of each indicia 136 is determined by comparing select reference points, such as arrival time 138, from each channel. A large diamond-shaped indicia 136c indicates the earliest arrival time, which in the embodiment shown is the arrival time 138c for channel three. A smaller diamond-shaped indicia 136d indicates the next earliest arrival time, which in FIG. 9 is the arrival time 138d for channel three. The remaining indicia 136a, 136b, and 136e are circular.

In addition to varying in shape, the indicia 136 may also vary in color, with the color a function of the quality number QN of the selected beat from the corresponding channel. In one embodiment, a green indicia represents a QN of 2, and yellow indicia represents a QN of 1, and a red indicia represents a QN of 0.

FIG. 9 further includes isochrone lines 140 indicating contours of waveform arrival times to the electrodes. Also included in FIG. 9 is an arrow 142 indicating the direction to the site of origin with respect to the electrode array.

In one embodiment, the displays of FIGS. 8 and 9 are displayed side-by-side in a single video monitor. Thus, a user can readily and easily view the beat and signal quality as well as other data relevant to the data received.

The embodiments described above are largely aimed at using the invention in cardiac procedures. However, the invention is applicable to various applications, including electrophysiology systems. For example, the invention is applicable to any processor-based system that must select a single multi-channel time-aligned set of waveforms from a group of sequentially captured multi-channel waveforms. For example, by selecting a quality metric other the $T_{md}-T_{id}$ value discussed above, the method can be extended to other applications where signal repeatability and/or consistency is an indication of signal and/or channel quality.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention.

What is claimed is:

1. A system for analyzing electrical signals in biological tissue, the system comprising:

a catheter having a proximal end and a distal end, said catheter having an array of at least two electrodes at the distal end, the electrodes detecting said electrical signals emanating from a site of origin and providing relayed signals representative of the electrical signals detected at the electrode position, wherein each electrode has an electrical channel along which the electrode transmits relayed signals to the receiver;

a receiver coupled to the catheter and receiving the relayed signals provided by the electrodes; and a processor for processing the relayed signals received from the receiver into waveforms and computing a quality of the relayed signals as a result of said processing, wherein the processor categorizes the relayed signals into beat signals when the biological tissue is heart tissue and wherein the processor selects a set of contemporaneous beat signals, said contemporaneous set comprising one beat signal from each of two or more channels, to comprise an aligned beat signal.

2. The system of claim 1, wherein the processor computes a channel quality and a beat signal quality, said channel quality and said beat signal quality comprising the relayed signal quality.

3. The system of claim 1, wherein the electrical signal comprises a tachycardia signal, and wherein said processor selects from a channel the set of beat signals that are most closely clustered, determines a quality metric for each selected beat signal, averages the quality metrics of the selected beat signals, and determines a channel quality as a function of said quality metrics and average quality metric.

4. The system of claim 3, wherein said processor determines a quality factor for one or more beat signals as a function of the proximity of the quality metric of the beat signal to the average quality metric for the channel.

5. The system of claim 4, wherein said processor calculates an aligned beat signal quality for at least one aligned beat signal as a function of the quality factors of the beat signals comprising the aligned beat signal.

6. The system of claim 5, wherein said processor calculates the aligned beat signal quality as the sum of the quality factors of the beat signals comprising the aligned beat signal.

7. A system for analyzing electrical signals in the heart, the system comprising:

a catheter having a proximal and a distal end, said catheter having an array of two or more electrodes at the catheter distal end, said electrodes detecting electrical signals emanating from a site of origin and providing relayed signals representative of the electrical signals detected at the electrode position;

a receiver for receiving the relayed signals detected by the electrodes; each relayed signal provided from a corresponding electrode to the receiver via a channel;

a processor for processing the relayed signals into beat signals, and computing a quality for one or more of the relayed signals; and a display for interactively displaying the quality of the relayed signals, wherein said display comprises a plurality of quality representations, wherein each quality representation displays the quality of a relayed signal from a particular electrode, wherein one or more quality representations each displays a beat signal quality and a channel quality for the corresponding relayed signal, wherein one or more quality representations each comprises a numerical readout of the computed quality of the corresponding relayed signal.

8. The system of claim 7, wherein one or more quality representations each comprises a selectively variable color, wherein variances in the selectively variable color correspond to variances in the computed quality of the corresponding relayed signal.

9. In a system for detecting electrical signals within biological tissue, said system having a multi-electrode catheter relaying electrical signals to multiple electrode channels, a method of determining the quality of the relayed signals, the method comprising the steps of:

(a) receiving relayed signals from one or more electrode channels; and (b) calculating a quality metric for one or more relayed signals, the quality metric related to one or more selected characteristics of the relayed signal.

10. The method of claim 9, comprising the further step of:

(c) displaying an indicator of the quality metric of one or more relayed signals.

11. The method of claim 9, including the further steps of:

(d) determining a channel quality for one or more electrode channels.

12. The method of claim 10, including the further step of:

(e) calculating an average quality metric for one or more electrode channels; and (f) determining a channel quality for one or more electrode channels, wherein said channel quality is calculated as the percentage of relayed signals for a particular electrode channel whose quality metric is within a selected range of the average quality metric for that electrode channel.

13. The method of claim 11, including the further step of:

(g) displaying an indicator of the determined channel quality percent of one or more channels.

14. The method of claim 9, including the further step of:

(h) determining a quality of one or more relayed signals, said signal quality determined as a function of the proximity of the quality metric of the particular relayed signal to the average quality metric for the electrode channel of the relayed signal.

15. The method of claim 9, wherein the biological tissue is heart tissue, and including the further steps of:

(i) categorizing one or more relayed signals each into a corresponding beat signal;

(j) determining the initial downslope and maximum downslope for each beat signal; and wherein the quality metric of a relayed signal comprises the time difference between the initial downslope and the maximum downslope of the corresponding beat signal.

16. The method of claim 15, including the further steps of:
(k) calculating an average quality metric for one or more electrode channels; and
(l) determining a channel quality for one or more electrode channels.

17. The method of claim 15, wherein the electrical source is a tachycardia source, and including the further step of:
(m) selecting the group of beat signals with the most tightly clustered quality metrics for each channel;
(n) calculating an average quality metric for the most tightly clustered group for each channel; and
(o) determining a channel quality for each channel as a function of the beat signal quality metrics and the average quality metric.

18. The method of claim 17, wherein said channel quality is calculated as the percentage of beat signals for a particular channel whose quality metric is within a selected time interval of the average quality metric for that channel.

19. The method of claim 17, including the further step of:
(p) assigning a quality number to at least one beat signal, said quality number determined as a function of the proximity of the quality metric of the particular beat to the average quality metric for the corresponding channel.

20. The method of claim 19, including the further steps of:
(q) determining at least one set of aligned beat signals from two or more channels; and
(r) calculating an aligned beat quality for the aligned beat set.

21. The method of claim 20, wherein said aligned beat quality is an aligned beat quality number, and said aligned quality number is equal to the sum of the quality numbers from each beat signal in the aligned beat set.

22. The method of claim 20, including the further steps of:
(s) selecting a representative aligned beat set, said representative aligned beat set being the aligned beat set with the highest aligned quality number; and
(t) displaying representations of the beat signal quality metrics and channel quality for the representative aligned beat set.

23. The method of claim 22, including the further step of:
(u) displaying representations of the beat waveforms of the representative aligned beat set.

24. In a system for detecting electrical signals within biological tissue, said system having at least one electrode relaying a series of electrical beat signals to an electrode channel, a method of analyzing the relayed beat signals, the method comprising the steps of:
(a) receiving the relayed beat signal;
(b) determining a signal parameter for at least two relayed signal beats, the signal parameter related to one or more selected characteristics of the relayed beat signal wherein the signal parameter comprises a quality metric of the relayed beat signals; and
(c) selecting from the relayed beat signals a group of relayed beat signals with the most consistent signal parameter.

25. The method of claim 24, including the further step of:
(d) calculating the average quality metric of the selected group of relayed beat signals; and
(e) determining a quality of one or more relayed beat signals, said signal quality determined as a function of the proximity of the quality metric of the particular relayed beat signal to the average quality metric for the electrode channel of the relayed beat signals.

* * * * *